United States Patent
Israeli et al.

(10) Patent No.: US 11,657,897 B2
(45) Date of Patent: May 23, 2023

(54) DENOISING ATAC-SEQ DATA WITH DEEP LEARNING

(71) Applicant: NVIDIA Corporation, Santa Clara, CA (US)

(72) Inventors: Johnny Israeli, San Jose, CA (US); Nikolai Yakovenko, Palo Alto, CA (US)

(73) Assignee: NVIDIA Corporation, Santa Clara, CA (US)

(*) Notice: Subject to any disclaimer, the term of this patent is extended or adjusted under 35 U.S.C. 154(b) by 1180 days.

(21) Appl. No.: 16/236,797

(22) Filed: Dec. 31, 2018

(65) Prior Publication Data

US 2020/0211674 A1    Jul. 2, 2020

(51) Int. Cl.

| | |
|---|---|
| *C12Q 1/68* | (2018.01) |
| *G06N 3/08* | (2023.01) |
| *G16B 20/30* | (2019.01) |
| *G16B 40/00* | (2019.01) |
| *G16B 30/00* | (2019.01) |
| *G16B 25/00* | (2019.01) |
| *G16B 5/20* | (2019.01) |
| *C12Q 1/6869* | (2018.01) |
| *G16B 25/10* | (2019.01) |
| *G16B 40/10* | (2019.01) |

(52) U.S. Cl.
CPC ........... *G16B 25/00* (2019.02); *C12Q 1/68* (2013.01); *G06N 3/08* (2013.01); *G16B 5/20* (2019.02); *G16B 20/30* (2019.02); *G16B 40/00* (2019.02)

(58) Field of Classification Search
CPC ........ G16B 25/00; G16B 20/30; G16B 40/00; G16B 5/20; C12Q 1/68; G06N 3/08
USPC ........................................................... 702/19
See application file for complete search history.

(56) References Cited

U.S. PATENT DOCUMENTS

| | | |
|---|---|---|
| 9,922,285 B1 | 3/2018 | Glode et al. |
| 10,059,989 B2 | 8/2018 | Giresi et al. |
| 2017/0249547 A1 | 8/2017 | Shrikumar et al. |
| 2018/0144261 A1 | 5/2018 | Wnuk et al. |

FOREIGN PATENT DOCUMENTS

| | | |
|---|---|---|
| WO | 2016201564 A1 | 12/2016 |
| WO | 2018006152 A1 | 1/2018 |
| WO | 2018094360 A2 | 5/2018 |

OTHER PUBLICATIONS

Nic Fishman and Sarah Gurev: "Denoising ATAC-seq with Convolutional Neural Networks", CS230: Deep Learning, Winter 2018, Stanford University, CA. (Year: 2018).*

(Continued)

*Primary Examiner* — G Steven Vanni
*Assistant Examiner* — Guozhen Liu
(74) *Attorney, Agent, or Firm* — Fisherbroyles LLP; Adam Whiting (57) ABSTRACT

The present invention provides methods, systems, computer program products that use deep learning with neural networks to denoise ATAC-seq datasets. The methods, systems, and programs provide for increased efficiency, accuracy, and speed in identifying genomic sites of chromatin accessibility in a wide range of tissue and cell types.

20 Claims, 5 Drawing Sheets

(56) References Cited

OTHER PUBLICATIONS

Naozumi Hiranuma, Scott Lundberg, Su-In Lee: "DeepATAC: A deep-learning method to predict regulatory factor binding activity from ATAC-seq signals", bioRxiv preprint doi: https://doi.org/10.1101/172767; this version posted Aug. 6, 2017 (Year: 2017).*

Wayback Machine, Internet Archive Report on Web Page "http://cs230.stanford.edu/projects_spring_2018/reports/8290367.pdf", https://archive.org/, Accessed Jan. 10, 2023. (Year: 2023).*

PCT/US2019/069093, International Search Report and Written Opinion of the International Searching Authority, dated Apr. 14, 2020.

Angermueller et al., "Deep learning for computational biology," Molecular Systems Biology 12:878, 1-16, published online Jul. 29, 2016.

Corces et al., "Lineage-specific and single-cell chromatin accessibility charts human hematopoiesis and leukemia evolution," Nature Genetics, vol. 48, No. 10, pp. 1193-1203 and online methods sections, Oct. 2016.

Alasoo et al., "Shared genetic effects on chromatin and gene expression indicate a role for enhancer priming in immune response," Nature Genetics, vol. 50, Mar. 2018, pp. 424-431.

Ou et al., "ATACseqQC: a Bioconductor package for post-alignment quality assessment of ATAC-seq data," BMC Genomics (2018) 19:169; https://doi.org/10.1186/s12864-018-4559-3.

Meyer et al., "Identifying and mitigating bias in next-generation sequencing methods for chromatin biology," Nature Reviews: Genetics, vol. 15, No. 11, Nov. 1, 2014, pp. 709-721.

Newman et al., "Robust enumeration of cell subsets from tissue expression profiles," Nature Methods, vol. 12, No. 5, Mar. 30, 2015, pp. 453-457.

Buenrostro et al., "Transposition of native chromatin for fast and sensitive epigenomic profiling of open chromatin, DNA-binding proteins and nucleosome position," Nature Methods, Published Online Oct. 6, 2013 DOI:10.1038/NMETH.2688.

Buenrostro et al., "Integrated Single-Cell Analysis Maps the Continuous Regulatory Landscape of Human Hematopoietic Differentiation," Cell 173, 1-14, May 31, 2018.

Chen et al., "ATAC-see reveals the accessible genome by transposase-mediated imaging and sequencing," Nature Methods. Dec. 2016 ; 13(12): 1013-1020. doi:10.1038/nmeth.4031.

Daugherty et al., "Chromatin accessibility dynamics reveal novel functional enhancers in C elegans," Genome Res. 2017 27: 2096-2107; originally published online Nov. 15, 2017.

Hiranuma et al., "DeepATAC: A deep-learning method to predict regulatory factor binding activity from ATAC-seq signals," bioRxiv preprint first posted online Aug. 6, 2017; doi: http://dx.doi.org/10.1101/172767.

Kelley et al., "Basset: learning the regulatory code of the accessible genome with deep convolutional neural networks," Genome Res. 2015 26:990-999.

Koh et al., "Denoising genome-wide histone ChIP-seq with convolutional neural networks," Bioinformatics, 33, 2017, i225-i233; doi: 10.1093/bioinformatics/btx243.

Poplin et al., "Creating a universal SNP and small indel variant caller with deep neural networks," bioRxiv preprint first posted online Dec. 14, 2016; doi: http://dx.doi.org/10.1101/092890.

Schep et al., "chromVARar: inferring transcription-factor-associated accessibility from single-cell epigenomic data," Nature Methods, published online 21 2017; doi:10.1038/nmeth.4401.

Thibodeau et al., "A neural network based model effectively predicts enhancers from clinical ATAC-seq samples," www.nature.com/ScientificReports (2018) 8:16048 | DOI:10.1038/s41598-018-34420-9; published online: Oct. 30, 2018.

Zhou et al., "Predicting effects of noncoding variants with deep learning-based sequence model," Nature Methods, 12 (10): 931-934; published online Aug. 24, 2015; doi:10.1038/nmeth.3547.

Israeli, "Deep Learning for Shallow Sequencing," presented at GTC Silicon Valley, Session S8602, Mar. 2018.

Fishman and Gurev, "Denoising ATAC-seq with Convolutional Neural Networks," downloaded from Mar. 25, 2022 from "Past Projects" website (http://cs230.stanford.edu/past-projects/#spring-2018) for Stanford University CS230 class.

* cited by examiner

FIG. 5

DENOISING ATAC-SEQ DATA WITH DEEP LEARNING

FIELD OF THE INVENTION

The present disclosure relates generally to methods and systems for using deep learning to denoise data obtained from ATAC-seq measurements.

BACKGROUND OF THE INVENTION

The human genome is the complete set of nucleic acid sequences for humans, encoded as DNA within the 23 chromosome pairs in cell nuclei and in a small DNA molecule found within individual mitochondria. The human genome consists of 6 billion base pairs that include both protein-coding DNA genes and noncoding DNA. The Human Genome Project published the first complete sequence of an individual human genome in 2001. Currently, thousands of human genomes have been completely sequenced, and many more have been mapped at lower levels of resolution. The resulting data are used worldwide in biomedical science, anthropology, forensics, and other branches of science. There is a widely held expectation that genomic studies will lead to advances in the diagnosis and treatment of diseases, and to new insights in many fields of biology, including human evolution.

Although the sequence of the human genome has been determined, a vast majority of it is still not fully understood. There are an estimated 19,000-20,000 human protein-coding genes, but these gene sequences account for only about 1.5% of the genome. Much of the rest is non-coding DNA has undetermined biochemical function but is believed to be crucial to the regulation of gene expression, the organization of chromosome architecture, and the control of epigenetic inheritance. For example, many non-coding DNA sequences are known to act as genetic "switches," also called enhancers, that regulate when and where the protein encoding genes are turned-on and off.

ATAC-seq (Assay for Transposase-Accessible Chromatin using sequencing) is a technique used to identify areas of chromatin accessibility within the genome. These areas of chromatin accessibility tend to be involved in genomic regulation—e.g., sites of regulatory protein binding. It is believed that many disease states arise due to mutations or epigenetic modifications at such regulatory sites, so developing methods to identify is critical. ATAC-seq was first described in Buenrostro et al., "Transposition of native chromatin for fast and sensitive epigenomic profiling of open chromatin, DNA-binding proteins and nucleosome position," Nature Methods. 10 (12): 1213-1218 (hereinafter "Buenrostro 2013"). The technique uses a mutant transposase enzyme that essentially cleaves and tags the genomic DNA located at regions of chromatin accessibility. ATAC-seq to map chromatin accessibility has many advantages over other techniques (e.g., MNase-seq, DNase-seq, ChIPs) used to map chromatin accessibility, most significantly: (a) at least 1000-fold lower amount of biological sample needed, and (b) much faster throughput—3 hours—rather than days. The relative efficiency and speed ATAC-seq make it one of the most promising new techniques for identifying and understanding the genomic features that lead to cancer. ATAC-seq datasets, however, still are extremely large and requiring intensive processing to analyze. Typically, the ATAC-seq dataset includes tens of millions of NGS reads which are expensive to obtain and process. Additionally, although relatively small, the amounts of sample required still make it difficult to study isolated cell-types (e.g., human cancer samples) from individuals. Thus, there remains a need for improved methods that further decrease the cost, processing time, and sample requirements of ATAC-seq analysis.

SUMMARY OF THE INVENTION

The present disclosure provides methods, systems, and a computer program product for denoising ATAC-seq dataset using a neural network. It is a surprising result of the present disclosure that a denoising process employing a convolutional neural network (CNN) architecture (e.g., three convolutional layers with no recurrent layer) can transform a suboptimal ATAC-seq dataset (e.g., only 5 million ATAC-seq reads) and output a denoised ATAC-seq dataset equivalent to a dataset obtained with up to 5× more reads. The effect of this denoising process is significant reduction in the time and cost of performing an ATAC-seq experiment. Furthermore, it is a surprising advantage of the neural network employed in the methods, systems, and computer program products of the present disclosure that the significant improvements of denoising are observed when carried out on an ATAC-seq dataset obtained from a cell-type or tissue type different from that used to train to the neural network.

In some embodiments, the present disclosure provides a method comprising:

partitioning an ATAC-seq dataset into a plurality of segments representing a genome, wherein the segments comprise ATAC-seq counts and exclude base identity at each base pair position; and transforming the segments with a neural network that sums the ATAC-seq counts of each of the plurality of segments with a convolutional layer output.

In some embodiments, the method is carried out wherein the segments have a length of about 1000 bp to about 25,000 bp.

In some embodiments, the method is carried out wherein the neural network comprises at least three successive convolutional layers followed by a residual connection that sums the ATAC-seq counts of each segment input with the final convolutional layer output. In some embodiments, each convolutional layer and the residual connection is followed by an ReLU layer. In some embodiments, the convolutional layers have a receptive field size of 100 to 10,000. In some embodiments, the convolutional layers use a number of filters selected from 1 to 100.

In some embodiments, the method is carried out wherein the neural network comprises 3 successive convolutional layers of receptive field size 100, 100, and 300, respectively, and using 15, 15, and 1 filters, respectively.

In some embodiments, the method further comprises training the neural network, wherein training comprises:

partitioning a suboptimal ATAC-seq dataset and a model ATAC-seq dataset into a plurality of segments representing a genome, wherein the segments comprise ATAC-seq counts and exclude base identity at each base pair position; and transforming the segments of the suboptimal ATAC-seq dataset with the neural network, using a loss function to compare the neural network output to the model ATAC-seq dataset segments, and adjusting the neural network until the loss function is minimized.

In some embodiments of the method further comprising training the neural network, the method is carried out wherein the loss function is a mean square error loss function; optionally, wherein the loss function comprises a weighted sum of a mean square error loss function and a Pearson's correlation loss function.

In some embodiments of the method further comprising training the neural network, the model ATAC-seq dataset relative to the suboptimal ATAC-seq dataset comprises at least 4-fold increased number of reads of ATAC-seq counts.

In some embodiments, the present disclosure provides a system comprising:

a processor, a memory device, and a denoising engine executable on the processor according to software instructions stored in the memory device, wherein the denoising engine is configured to:

partition an ATAC-seq dataset into a plurality of segments representing a genome, wherein the segments comprise ATAC-seq counts and exclude base identity at each base pair position; and transform the segments with a neural network that sums the ATAC-seq counts of each of the plurality of segments with a convolutional layer output.

In some embodiments of the system, the denoising engine is configured with a neural network comprising at least three successive convolutional layers followed by a residual connection that sums the ATAC-seq counts of each segment input with the final convolutional layer output. In some embodiments, each convolutional layer and the residual connection is followed by an ReLU layer. In some embodiments, the convolutional layers have a receptive field size of 100 to 10,000. In some embodiments, the convolutional layers use a number of filters selected from 1 to 100. In some embodiments of the system, the neural network comprises 3 successive convolutional layers of receptive field size 100, 100, and 300, respectively, and using 15, 15, and 1 filters, respectively.

In some embodiments, the system further comprises:

a training engine executable on the processor according to software instructions stored in the memory device, wherein the training engine is in communication with the denoising engine and is configured to:

partition a suboptimal ATAC-seq dataset and a model ATAC-seq dataset into a plurality of segments representing a genome, wherein the segments comprise ATAC-seq counts and exclude base identity at each base pair position; and transform the segments of the suboptimal ATAC-seq dataset with the neural network, using a loss function to compare the neural network output to the model ATAC-seq dataset segments, and adjusting the neural network until the loss function is minimized.

In some embodiments, the present disclosure provides a non-transitory computer-readable medium comprising instructions for denoising an ATAC-seq dataset that, when executed by a processor, cause the processor to perform one or more steps comprising:

partitioning an ATAC-seq dataset into a plurality of segments representing a genome, wherein the segments comprise ATAC-seq counts and exclude base identity at each base pair position; and transforming the segments with a neural network that sums the ATAC-seq counts of each of the plurality of segments with a convolutional layer output.

In some embodiment, the non-transitory computer-readable medium further comprises instructions for:

partitioning a suboptimal ATAC-seq dataset and a model ATAC-seq dataset into a plurality of segments representing a genome, wherein the segments comprise ATAC-seq counts and exclude base identity at each base pair position; and transforming the segments of the suboptimal ATAC-seq dataset with the neural network, using a loss function to compare the neural network output to the model ATAC-seq dataset segments, and adjusting the neural network until the loss function is minimized.

In the various embodiments of the system and non-transitory computer-readable medium, it is contemplated that the various features useful in the method for denoising ATAC-seq data described above and elsewhere herein, including the neural network architecture features and training features, can be used as features in the system and non-transitory computer-readable medium.

DETAILED DESCRIPTION

For the descriptions provided herein and in the appended claims, the singular forms "a", and "an" include plural referents unless the context clearly indicates otherwise. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Thus, where the stated range includes one or both of these limits, ranges excluding (i) either or (ii) both of those included limits are also included in the invention. For example, "1 to 50," includes "2 to 25," "5 to 20," "25 to 50," "1 to 10," etc.

One should appreciate that the disclosed techniques provide many advantageous technical effects including improving the scope, accuracy, compactness, efficiency and speed of predicting DNA accessibility in a genomic sample using a neural network. It should also be appreciated that the following specification is not intended as an extensive overview, and as such, concepts may be simplified in the interests of clarity and brevity.

Generally, the nomenclature used herein, and the techniques and procedures described herein include those that are well understood and commonly employed by those of ordinary skill in the art, such as the common techniques and methodologies for ATAC-seq data acquisition and analysis described in Buenrostro 2013, and at the publicly available Encyclopedia of DNA Elements ("ENCODE") project consortium site (www.encodeproject.org).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

ATAC-Seq Experiments and Data Analysis

ATAC-seq (Assay for Transposase-Accessible Chromatin using sequencing) is a technique used to study areas of chromatin accessibility within the genome. Areas of chromatin accessibility are associated with the binding of regulatory proteins that facilitate genomic regulation. Thus, it is believed that the use of ATAC-seq to identify areas of chromatin accessibility within the genome can lead to new understandings of genomic regulatory problems lead to many diseases, such as cancers. As noted above, the ATAC-seq technique was first described in the Buenrostro 2013 publication (see also, Giresi et al., U.S. Pat. No. 10,059,989, issued Aug. 28, 2018, which is hereby incorporated herein by reference). The key feature of ATAC-seq technique is the use of a mutant transposase enzyme "Tn5" that efficiently cleaves DNA, with base pair precision, at regions of the genome that exhibit chromatin accessibility and simultaneous ligates specific identifiable sequences, called adapters, to the cleaved portions of DNA. The cleaved genomic DNA ligated to the adapter sequences are then isolated, amplified using PCR, and finally sequenced (or "read"). The number of DNA fragments that must be sequenced from an ATAC-seq experiment typically numbers in the millions. Thus, the ability to use high-throughput, next generation sequencing (NGS) technologies is critical to the success of an ATAC-seq experiment.

ATAC-seq datasets are extremely large including tens of millions of NGS reads at sites spanning the full length of a genome. A typical high-quality ATAC-seq dataset useful for analysis of chromatin accessibility requires obtaining at least 20 million (20 M) and preferably 50 million (50 M) of NGS reads (i.e., determining the sequence of 50 M DNA fragments), assigning each of those reads to its specific location on the genome with base pair ("bp") resolution, and then totaling up number of reads (i.e., the "ATAC-seq counts") at location. Thus, acquiring a high-quality dataset with 50 M reads is very costly.

Because ATAC-seq uses the Tn5 mutant transposase and genomic DNA from a cellular nucleus, the sequence reads that are made cannot be limited just one part of the genome. The whole of the genome must be accounted for in assigning the reads to locations and totaling the counts. Thus, processing the ATAC-seq dataset requires mapping the counts for each read to the full length of the genome at bp resolution. Once the ATAC-seq counts for all of the reads are mapped to the genome, the resulting dataset can be visualized as a histogram spanning its full length. In the case of the human genome, the histogram of an ATAC-seq dataset has ~3 billion bp along the x-axis and peaks corresponding to the number of ATAC-seq counts for each read on the y-axis.

The NGS reads from an ATAC-seq experiment, after elimination of duplicates, are each mapped, using the known genome sequence, to the specific position on the genome where transposition (or cutting) event took place. The number of ATAC-seq counts are assigned with base-pair resolution to each genomic position resulting in the ATAC-seq signal. The location of peaks in the ATAC-seq counts on the genome indicates a region where the chromatin DNA was accessible during the experiment. Regions at which significantly more ATAC-seq counts are identified are assigned as an ATAC-seq signal or "ATAC-seq peak-call." ATAC-seq peak calls indicate potential genomic regulatory elements, such as promoters, enhancers, insulators. In cases with sufficient ATAC-seq count data resolution, sub-regions within a ATAC-seq peak-call that exhibit a depleted ATAC-seq counts can be observed. These count-depleted sub-regions, often only a few base pairs long, can indicate the "footprint" of a DNA-binding protein bound to the genome.

Ideally, an ATAC-seq dataset provides for single bp resolution of the location of the ATAC-seq counts and peak-calls, which allows for identification of specific sequences involved in genome regulatory functions. Such resolution, however, typically such high-quality datasets require at least 20 M and preferably 50 M reads of ATAC-seq counts. The reasons for less than ideal or suboptimal ATAC-seq datasets include limited time resulting in fewer NGS reads (e.g., only 5 M), limited sample size resulting in fewer cells (e.g., <500 cells), and/or rare or low abundance of the sample type (e.g., cancer biopsy tissue). The ability to obtain increased signal-to-noise and well-resolved ATAC-seq counts and/or assignable ATAC-seq peak-calls from suboptimal ATAC-seq datasets thus would greatly facilitate improvements in and expansion of the use of ATAC-seq in solving problems related to human health.

Using Neural Networks to Denoise ATAC-Seq Data

The present disclosure provides deep learning techniques useful to denoise suboptimal ATAC-seq datasets, such as datasets including 5 M or fewer sequence reads, and thereby facilitating faster, more efficient, and more cost-effective use of ATAC-seq measurements to identify regions of chromatin accessibility across a wider range of sample types. The deep learning techniques are based on the use of neural network, such as a convolutional neural network (CNN), that has been trained to denoise suboptimal ATAC-seq datasets. Neural networks, and in particular CNNs, have found wide use for deep learning in a wide range of areas, most notably, image recognition, but also for noise reduction or denoising of large complex datasets.

Generally, the application of neural networks for deep learning tasks involves two steps: (1) training of the neural network, in which the adjustable weighting parameters (or "weights") of the neural network are "learned" using training examples; and (2) classifying the experimental data of interest using the trained (or optimized) neural network to provide some useful output.

Training a neural network to perform a task, such as denoising, involves a process in which the network architecture "learns" an optimal set of weighting parameters that result in the best fit (or mapping) of a training dataset (e.g., a low-quality or suboptimal ATAC-seq dataset) to a model dataset (e.g., a high-quality ATAC-seq dataset). This learning process typically involves an iterative stochastic gradient descent-based minimization through the space of weights. The training process thus typically uses a forward-propagation calculation for each training example, a measurement of the error between the computed and desired output, and then back-propagation through the network to update the weighting parameters.

Training a neural network to perform denoising, as contemplated herein, includes the more involved and time-consuming initial training, but also includes less time-consuming "transfer learning" training of a neural network that has previously been trained for a task. Transfer learning embodiments typically involve further training of a neural network without re-learning the complete set of adjustable weighting parameters. Transfer learning may be carried out by training a neural network (e.g., CNN) that has already been trained with a suboptimal dataset using a new and different type of dataset. For example, a neural network initially trained using ATAC-seq data obtained from a stomach tissue cells would be trained with a dataset obtained from heart tissue cells. Thus, the learning from training the neural network on stomach tissue data would be transferred in the training the neural network with heart tissue data. Because it does not require starting over from scratch in adjusting the weighting parameters, the training process involved in transfer learning is greatly reduced. Accordingly, it is contemplated in the methods of the present disclosure for denoising ATAC-seq data that the method further comprises training the neural network. In some embodiments, this further training corresponds to transfer learning using an ATAC-seq dataset from a different type of sample than was used in the original training of the neural network.

The methods, architectures, and systems for training a neural network, such as a CNN, and then using the trained neural network in embodiments for denoising ATAC-seq datasets are described in greater detail below, and further illustrated in the Figures and Examples.

Figure 1:
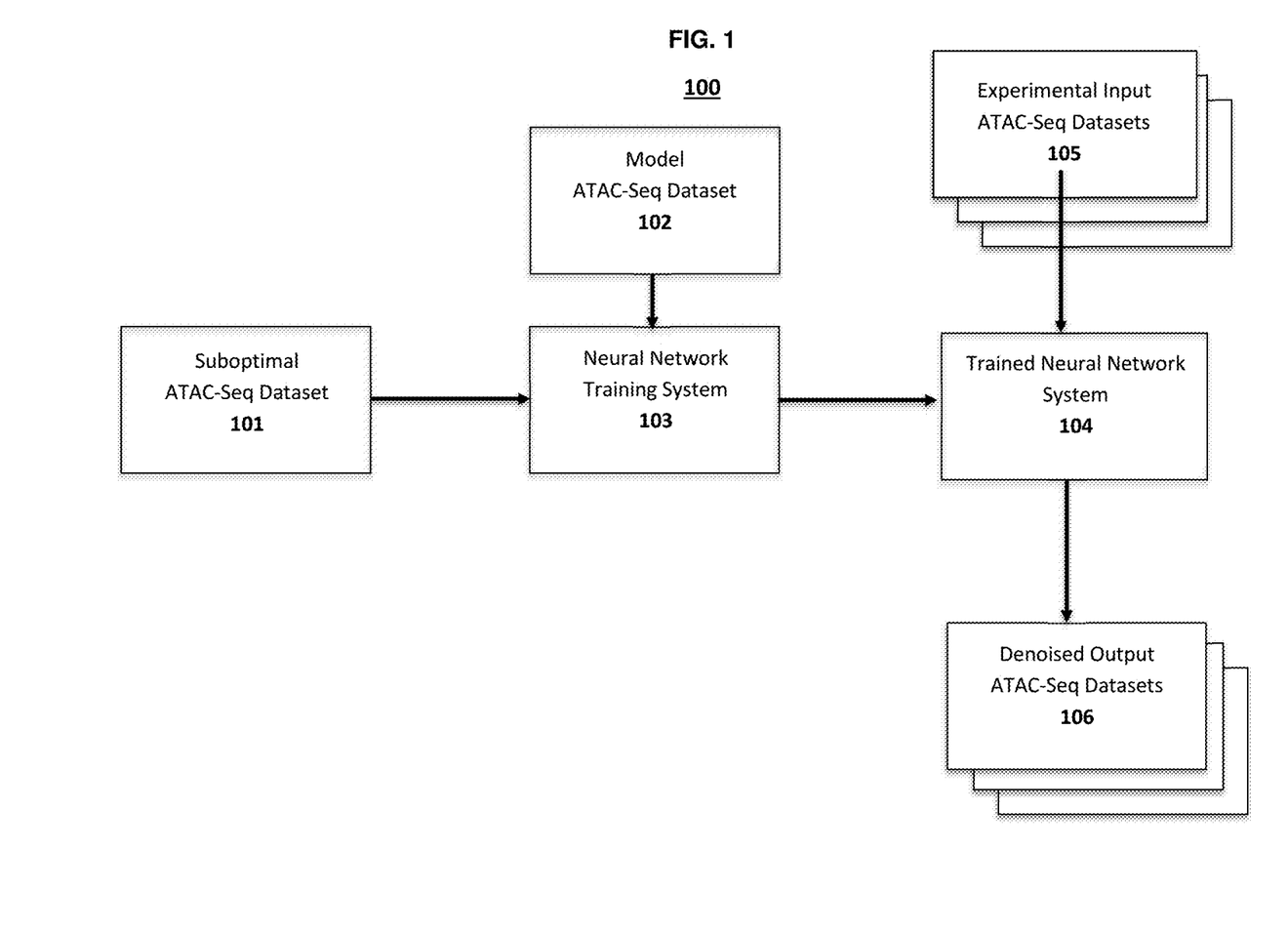
FIG. 1 depicts an overview flow diagram of exemplary operations for denoising an ATAC-seq dataset in accordance with embodiments of the present disclosure.

FIG. 1 illustrates the flow of operations for training a neural network to denoise an ATAC-seq dataset and using it to denoise experimental data (e.g., data not used in training). In the flow diagram 100 a suboptimal ATAC-seq dataset 101 and a high-quality model ATAC-seq dataset 102 are the initial input into a system comprising a neural network training system 103. The suboptimal 101 and model ATAC-seq datasets 102 are input into the neural network training system 103 and used to train the neural network for its desired denoising task. The parameters and architecture defining the initial configuration of the neural network, such as the number of convolution layers, receptive field sizes, and filters, are described in greater detail below and illustrated in FIG. 2.

The suboptimal and model ATAC-seq datasets 101 and 102 used in training comprise the ATAC-seq counts at each bp position of a genome but excludes the sequence information (i.e., base identity or base-call) for each bp position of the genome. Thus, a typical ATAC-seq dataset obtained from human cell samples which includes ATAC-seq counts for the complete 3 billion bp of the human genome can be used without including the informational overlay of the human genome sequence. This feature of being able to use an ATAC-seq dataset at bp resolution that excludes sequence information yet provides robust denoising results provides a great advantage in time, cost, and efficiency to the methods and systems of the present disclosure.

Because the methods and systems use ATAC-seq datasets that include ATAC-seq counts (and optionally, ATAC-seq peak-calls) at single bp resolution across the genome, it is not necessary to prepare the dataset by binning (or averaging) the data across defined regions of the genome (e.g., binning 25 bp regions into a single data point). Furthermore, the ability to train the neural network with full resolution datasets and across the full-length of a genome provides a more robust neural network. Accordingly, in some embodiments of the present disclosure the method and systems can be used wherein the ATAC-seq dataset includes ATAC-seq counts at each base pair position.

The discovery that the present neural network-based methods of denoising ATAC-seq datasets are sequence information independent is particularly surprising. This discovery provides further advantages in time, cost, and efficiency to the robust methods and systems for denoising described herein because the further processing required to map the sequence information onto the ATAC-seq dataset and carry it through the training and/or denoising process is not required. Accordingly, in some embodiments of the present disclosure the method and systems of denoising ATAC-seq data can be used wherein the ATAC-seq dataset excludes base identity at each base pair position.

Furthermore, the exclusion of sequence information provides the additional advantage of making the training and/or denoising processes independent of sample type. Differences in sequence information that exist between different cell-types are not included in the training or experimental datasets. This allows a neural network trained on ATAC-seq datasets from one cell-type to be used effectively in the process and systems denoising an experimental ATAC-seq dataset from another cell-type. This advantageous effect is illustrated in Example 2 described below. Accordingly, in some embodiments of the present disclosure the method and systems of training denoising ATAC-seq data can be used wherein the initial ATAC-seq dataset is from experiments performed on a sample from a cell-type or tissue and the suboptimal and model ATAC-seq datasets used to train the neural network (e.g., CNN) are from experiments performed on samples from a different cell-type or tissue sample.

Thus, in some embodiments of the methods and systems for training and/or denoising ATAC-seq dataset, the datasets input into the neural network training system or trained neural network comprise ATAC-seq counts (and optionally, ATAC-seq peak-calls) at each base pair position and exclude base identity at each base pair position.

It is contemplated that the neural network training system 103 accepts input of a suboptimal dataset 101, that is of lower quality in some respect compared to the model ATAC-seq dataset 102. For example, the suboptimal dataset can have an average number of ATAC-seq reads, N is selected from about 1 M, about 2.5 M, about 4 M, about 5 M, about 7.5 M, or about 10 M. In contrast, the model dataset 102 can have an average number of ATAC-seq reads that is at least 10× the number of reads in suboptimal dataset. In some embodiments, the model ATAC-seq dataset 102 comprises on average ~50 M ATAC-seq reads, or an average number of reads increased relative to the suboptimal dataset by at least 2-fold, at least 4-fold, at least 10-fold, or at least 25-fold.

As noted above, even the suboptimal ATAC-seq dataset can be extremely large, typically including an average of ~5 M adapter sequence reads at bp resolution spanning the full-length of the 3 billion bp human genome. The model ATAC-seq dataset 102 and the experimental input ATAC-seq datasets 105 can be even larger. Due to the large size of these datasets, in some embodiments of the methods and systems of training and denoising the suboptimal ATAC-seq dataset 101 and/or model ATAC-seq dataset 102 is partitioned into a plurality of segments representing the genome from which the data is obtained. Typically, the partitioning of the dataset occurs before input into the neural network trained system 103 or the trained neural network system 104.

The length of the partitioned segments can vary depending on the neural network architecture and associated computing power, however typically is selected from about 1000 bp, about 2500 bp, about 4000 bp, about 5000 bp, about 7500 bp, about 10,000 bp, or about 25,000 bp. In exemplary embodiments described elsewhere herein, the dataset is partitioned into 4000 bp segments. In some embodiments the segments are of equal size, and/or non-overlapping. In some embodiments, the partitioned segments are non-overlapping of equal size and span the full-length of a genome.

As used herein, the term "genome" is used to refer to a full genome or a portion of a genome. Accordingly, in some embodiments of the methods of training and/or denoising of the present disclosure are carried out on ATAC-seq datasets partitioned into segments representing a genome, wherein the genome is a complete, full-length genome or only a desired portion of a genome, e.g., a single chromosome.

In the training method of the present disclosure, the model ATAC-seq dataset 102 is input into the neural network training system 103 and used as the model data to which the suboptimal data is fit following its transformation by the neural network. As such, the model dataset 102 typically includes on average the number of ATAC-seq reads that provides the desired denoising level for the suboptimal ATAC-seq dataset. The model ATAC-seq dataset 102 also is at bp resolution excluding sequence information and partitioned into segments that represent the same genome as used in partitioning the suboptimal training dataset 101. Typically, the model and suboptimal datasets are obtained from the sample type using the same ATAC-seq experimental conditions. In some embodiments, the suboptimal dataset 101 can be prepared from the model dataset 102 by removing or holding out some portion of the data from a model dataset.

As described above, the neural network training process carried out by the training system 103 includes mapping or fitting the suboptimal data transformed by the neural network to the model dataset using a loss function. Accordingly, the loss function is an important feature of the training process embodied in the neural network system 103 as it is used to calculate the errors between the transformed suboptimal dataset 101 and the model dataset 102. By minimizing this loss function, e.g., through a stochastic gradient descent involving iterative adjustment of the neural network weight parameters, the neural network training system 103 produces a trained neural network. It is the trained neural network as part of the trained neural network system 104 that is optimized for use with an input experimental ATAC-seq dataset 106 to produce a denoised dataset 106.

A range of loss functions useful in training neural networks, such as CNNs, are known in the art and can be used in the denoising methods and systems of the present disclosure. It is a surprising advantage of the present disclosure, however, that robust training of a neural network, such as a CNN, for the task of denoising ATAC-seq data can be achieved using a mean square error loss function. In some embodiments, a loss function useful in training the neural network can comprise a mean square error loss function. Additionally, in some embodiments, the loss function can comprise a weighted sum of a mean square error loss function and a Pearson's correlation loss function.

Neural Network Architecture

The architecture of a neural network, such as a CNN, is critical to its ability to be trained (or learn) a specific predictive function, such as denoising an ATAC-seq dataset. The primary features of the neural network architecture that must be established prior to training include the number of neural layers, the operation performed by each layer, and the connectivity between the layers. Generally, the neural layers include one or more associated "filters" that perform a computational transformation of the input data, and each filter has an associated adjustable weighting parameter, sometimes referred to as "filter weights." The combination of filters and their weights determine the exact computational transformation performed (or filter applied) on the input data by the layer. It is the filter weighting parameters that are "learned" during the training process by minimizing the loss function. The final weighting values, which are set at the end of training, determine architecture (or configuration) of the trained neural network useful for denoising experimental ATAC-seq datasets.

Figure 2:
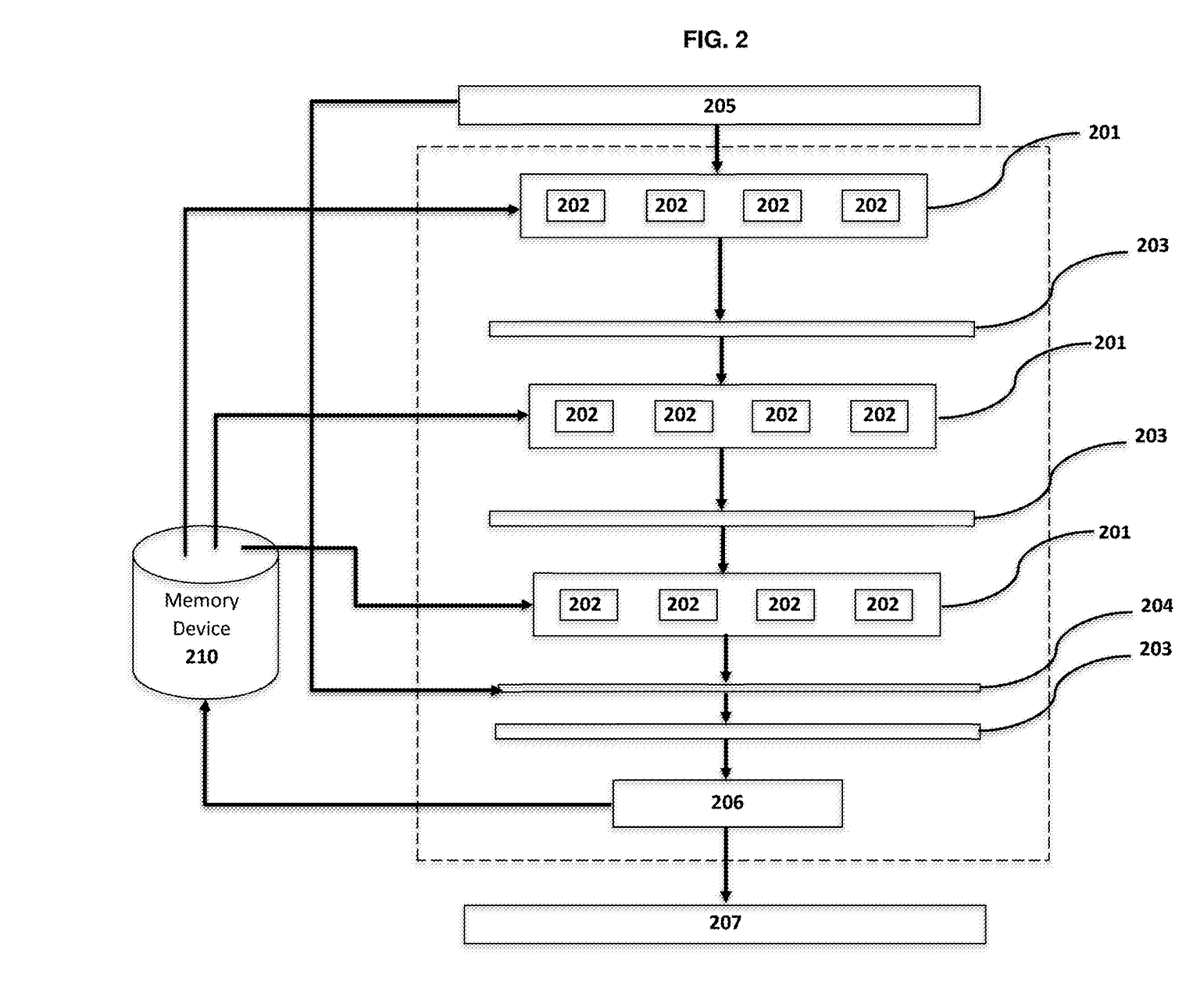
FIG. 2 depicts a block diagram of an exemplary neural network configured for use in denoising an ATAC-seq dataset in accordance with embodiments of the present disclosure.

FIG. 2 depicts an exemplary neural network having a CNN architecture that is useful in the methods and systems of the present disclosure. The input to the neural network 205 comprises a segment of an initial, typically suboptimal, ATAC-seq dataset that has been partitioned into segments that represent a genome. As described above, the suboptimal and experimental ATAC-seq datasets used in the methods of the present disclosure comprise ATAC-seq counts (and optionally, ATAC-seq peak-calls) at single bp resolution on a segment of the genome (e.g., 4000 bp) and exclude any information identifying the base (or sequence call) at the bp position.

In either training or using the trained neural network, the segment of the ATAC-seq dataset is received as input in a first convolutional layer 201 and undergoes a computation defined one or more of the weighted filters 202 associated with the first layer. The resulting output of the first layer is a convolution of the input dataset. Each of the convolutional layers can have a range receptive field sizes, typically between 100 and 1000. Similarly, the number of filters used in a layer can vary between the different layers. In the embodiments of the present disclosure a number of filters from 1 to 15 has been found to provide good denoising results and provide good computational efficiency.

After the convolutional layer, the transformed data output is acted on by a rectified linear unit or ReLU 203. The ReLU rectifies all negative values in the convoluted dataset to zero before it enters the next successive convolutional layer in the neural network. The exemplary architecture of FIG. 2 includes three convolutional layers 201 each of which is followed by a ReLU 203. The final convolutional layer 201, however, also is followed by a residual connection 204. This residual connection 204 after the final layer 201 performs a summing operation of the convolved dataset output from the final layer 201 with the original input dataset segment 205 before it is rectified by the final of the succession of ReLu 203.

During the training of the neural network, the output of the final ReLU of the neural network is a transformed dataset 206 that is input into a memory device 210 where a loss function calculates the accuracy (i.e., errors) of its mapping to the model ATAC-seq dataset. The error values calculated by the loss function in the memory device 210 are used to adjust the weights associated with one or more of the filters 201. Following adjustment of the weighting parameters, the suboptimal training dataset segment 205 is input into the neural network and transformation process carried out by the adjusted filters 202 in each of the convolutional layer 201 is repeated.

As noted above, it is contemplated that the methods for training a neural network useful in the denoising methods and systems can include transfer learning type training. Typically, in such embodiments the training datasets differ in some way from the datasets used to originally train the neural network. Accordingly, it may be determined that adjustments of the weighting parameters can be limited. For example, selected weights and/or selected filters can be held constant, while others are adjusted. In this way, transfer learning can train the neural network to work better in denoising with different types of datasets without complete re-training of the neural network.

Typically, the final trained neural network architecture is configured after numerous iterations of the training process when it is determined that further iterations fail to further reduce the loss function below some threshold. That is, the neural network is fully trained when the loss function is minimized. The architecture of the trained neural network, with its filter weights set at their optimal, trained values, can then be used most effectively to denoise an experimental ATAC-seq dataset.

Referring again to FIG. 2, when using a neural network to denoise an experimental input 205, the output dataset 206 transformed by the three layers of neural network is not fed back into the memory device 210 for fitting to the model dataset and then readjustment of the weighting parameters. Instead, a final denoised dataset 207 is output from the neural network denoising module.

In some embodiments of the methods and systems for denoising ATAC-seq datasets of the present disclosure, the neural network used is a completely convolutional neural network or CNN. As exemplified in FIG. 2, a CNN useful in the methods and systems for denoising can include a plurality of successive convolution layers with each convolution layer followed by a ReLU layer. In some of the embodiments of the denoising methods and systems of the present disclosure, the CNN does not include any fully connected or recurrent layers. Although, increasing the number of convolution layers in a neural network provides increased non-linearity and better accuracy in the resultant output, too many convolution layers results in increased computing time and energy with diminishing returns on accuracy. It is an advantage of the methods and systems using the neural network architecture of the present disclosure that robust denoising of extremely large ATAC-seq datasets can be achieved using relatively few convolution layers. Accordingly, in some embodiments, the neural network useful n the methods and systems of the present disclosure comprises at least three convolutional layers. In some embodiments, the number of convolutional layers is from 3 to about 100, from 3 to about 50, from 3 to 10, or even from 3 to 5.

Configuration of the neural network also requires defining the receptive field sizes for each of the plurality of convolution layers. In the embodiments of the present disclosure, useful receptive field sizes of the convolutional layers in the neural network are between about 50 and about 500. Once again, there is a trade-off in efficiency with increasing receptive field of the convolution layers. Accordingly, in some embodiments, the receptive field size of the convolution layers is from about 100 to about 300. Further, in some embodiments, one or more of the different convolution layers have different receptive field sizes. Generally, a larger receptive field facilitates convolution of a larger dataset input. As noted above, ATAC-seq datasets are extremely large, including millions of ATAC-seq counts at single bp resolution that span a genome—e.g., the 3 billion bp length of the human. Accordingly, it is contemplated that convolution layers of the neural networks useful in the methods and systems of the present disclosure have a receptive field size of at least 100, at least 300, at least 500, at least 1000, or at least 10,000. There is a trade-off in computational time and energy for denoising using very large receptive field sizes. Thus, in some embodiments, the plurality of convolution layers has receptive field sizes selected 100 to 10,000, 100 to 1000, 100 to 500, or 100 to 300.

It is contemplated that the receptive field size can vary across the plurality of convolution layers. For example, in one embodiment useful in the methods and systems for denoising the neural network has three convolutional layers, wherein the successive layers have a receptive field size of 100, 100, and 300, respectively.

As noted above, the number and size of filters present in each convolution layer is an important parameter in configuring the CNN architecture for use in denoising an ATAC-seq dataset is the. While an increased number of filters can often provide a more accurate CNN, it is a surprising result of the present disclosure that a CNN having robust performance in denoising ATAC-seq data can be achieved with as few as 15 filters in the intermediate convolution layers. Accordingly, in some embodiments of the methods and systems of the present disclosure, each convolution layer of the CNN uses a number of filters selected from 1 to 100, 1 to 50, 1 to 25, and 1 to 15.

In some embodiments, the number of filters configured in the plurality convolutional layers differs. Typically, the final layer uses one just filter in outputting the final denoised data. Accordingly, in one embodiment useful in the methods and systems for denoising the CNN has three convolutional layers, wherein the successive convolution layers have a receptive field size of 100, 100, and 300, respectively, and use a number of filters of 15, 15, and 1, respectively.

The size of the filters is also a factor in configuring the CNN for optimal performance in denoising ATAC-seq data. In the embodiments of the methods and systems of the present disclosure, the filters of the convolution layers have a size in the range of 100 to 500.

Another aspect of the CNN useful in the methods and systems of the present disclosure is that each convolution layer is followed by a rectified linear unit or ReLU layer. The ReLU layer sets any negative values in the convolved data output from the prior convolution layer to zero, thereby simplifying further convolutional computations, but without a significant effect on the quality of the denoised dataset. In some embodiments, the CNN comprises three convolution layers each followed by a ReLU layer. In one embodiment useful in the method and systems of the present disclosure, the CNN comprises three successive convolution layers each followed by a ReLU layer, wherein the receptive field sizes of the three successive convolution layers is 100, 100, and 300, respectively. Optionally, the three successive convolutional layers use 15, 15, and 1 filters respectively.

Finally, as noted in the exemplary features of FIG. 2, it is contemplated that a residual connection is included between the final convolution layer and its corresponding final ReLU layer of the neural network. The residual connection is configured to sum the counts of the input ATAC-seq counts with the final convolution layer output. This summing function carried out by the residual connection results in an output from the final layer of the neural network that better presents the denoised ATAC-seq dataset and/or better highlights the differences between the transformed output ATAC-seq dataset and the model ATAC-seq dataset during training. Accordingly, in some embodiments of the neural network architecture, the final ReLU layer is preceded by a residual connection that sums the counts of the input ATAC-seq counts with the final convolution layer output.

Thus, in one exemplary embodiment of the present disclosure, the methods and systems for training and denoising use a neural network architecture wherein the neural network (e.g., a CNN) comprises three successive convolutional layers of receptive field size 100, 100, and 300, respectively, and each using 15, 15, and 1 filters, respectively, where each convolutional layer is succeeded by an ReLU layer, wherein the final ReLU layer is preceded by a residual connection that sums the output of the final convolutional layer and the ATAC-seq counts of the input ATAC-seq dataset.

As noted above, the methods and systems for training and denoising disclosed herein for denoising ATAC-seq data provide surprising advantages over other denoising methods in the art. As noted above, the methods and systems utilize ATAC-seq datasets at bp resolution (i.e., without binning regions) that exclude bp sequence information, and are capable of denoising experimental ATAC-seq datasets from a wide-range of sample types, including sample types different from those used in the training ATAC-seq datasets.

Computer-Based Implementations of the Various Embodiments

The computations and data manipulations carried out within the neural network (e.g., a CNN) are beyond the capabilities of a human for purposes of denoising an ATAC-seq dataset from a genomic sample. Neural network training and use generally requires high-performance, energy efficient computer processors and is often carried out using graphics processing units (GPUs) or farms of GPUs. Accordingly, in some embodiments, the present disclosure provides a computing device configured to apply the neural network in a process for denoising the vast quantities of digital data associated with an ATAC-seq dataset.

Figure 3:
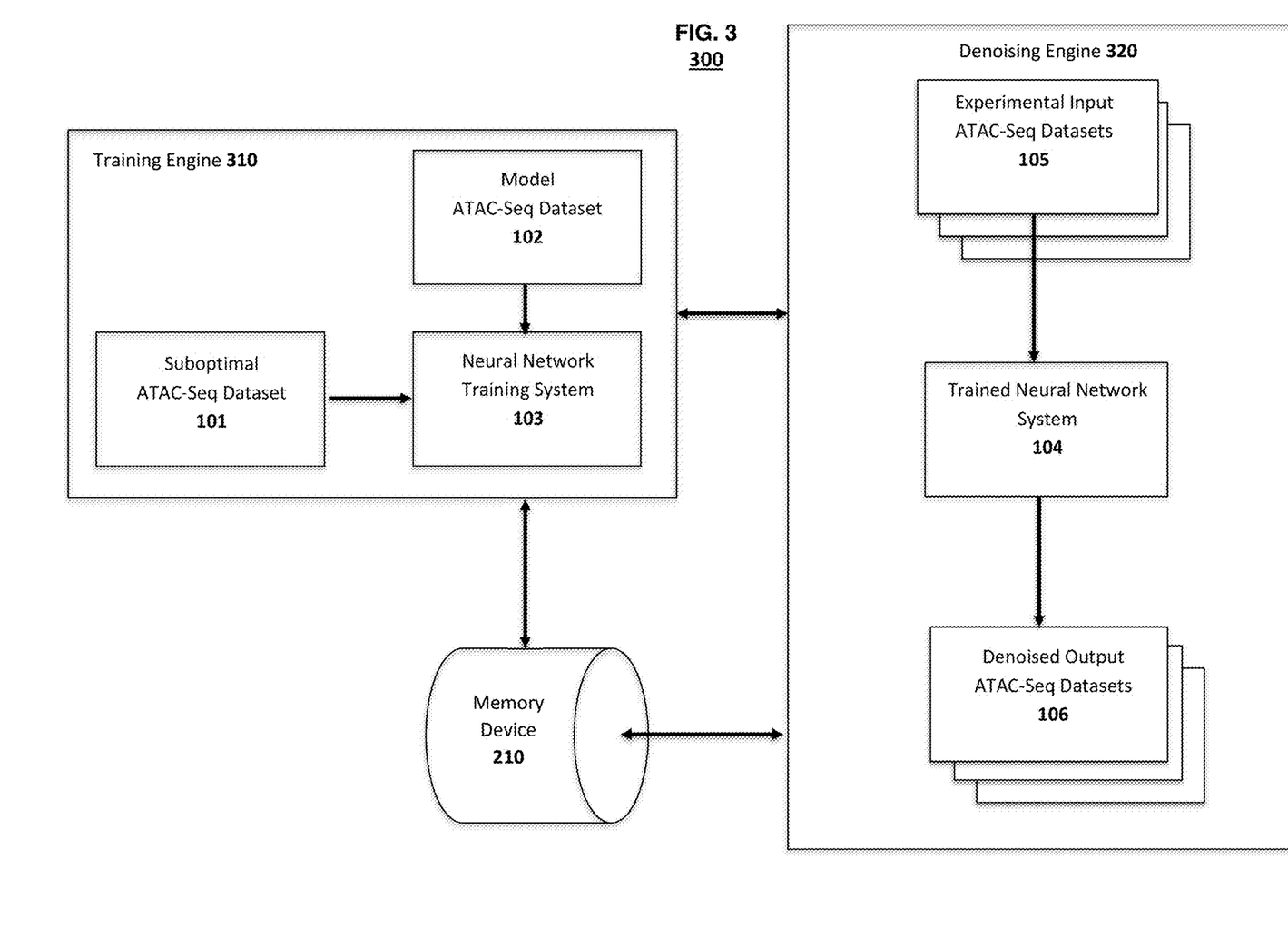
FIG. 3 depicts a block diagram of an exemplary system useful for denoising an ATAC-seq dataset in accordance with embodiments of the present disclosure.

FIG. 3 illustrates a block diagram of a computer-based system useful for training a neural network and using the trained neural network system to denoise experimental ATAC-seq datasets in accordance with embodiments of the present disclosure. In block diagram 300, the elements include a training engine 310 and a denoising engine 320. The training engine is configured to accept input of a suboptimal dataset 101 and a model dataset 102 from a memory device 210, which can comprise temporary memory and/or a persistent storage device. The training engine 310 configures and trains the neural network system 103, which can be stored in the memory device 210, using the suboptimal and model datasets. The function of the training engine results in an optimized neural network system 104 which can be stored in a memory device 210 such that it can be accessed and used by the denoising engine 320. The denoising engine 320 is configured to accept input of experimental ATAC-set datasets 105 and transform them, using the optimized neural network system 104, into denoised ATAC-seq datasets 106. The input of the experimental datasets 105 and the output of the denoised datasets 106 can be stored in the memory device 210. It is contemplated that the denoising engine can provide further computer-based treatment of the input and output datasets such as partitioning the datasets into non-overlapping segments and then reassembling the denoised segments to provide an output dataset covering the full-length of the genome or genome portion from which the data was obtained.

The various elements of FIG. 3, and the functions attributed to them, are described generally for ease of understanding. One skilled in the art will recognize that one or more of the functions ascribed to the various elements may be performed by any one of the other elements, and/or by an element not shown in the figure. Furthermore, it is contemplated that the elements may be configured to perform a combination of the various functions described above as supported by the various embodiments described elsewhere herein. Accordingly, the description of a train g engine 310, a denoising engine 320, a and a memory device 210 are intended to include any suitable combination of computing devices, including servers, interfaces, systems, databases, agents, peers, engines, controllers, modules, or other types of computing devices operating individually or collectively to perform the functions ascribed to the various elements. Further, one skilled in the art will recognize that one or more of the functions of the system of FIG. 3 described herein may be performed within the context of a client-server relationship, such as by one or more servers, one or more client devices (e.g., one or more user devices) and/or by a combination of one or more servers and client devices.

Figure 4:
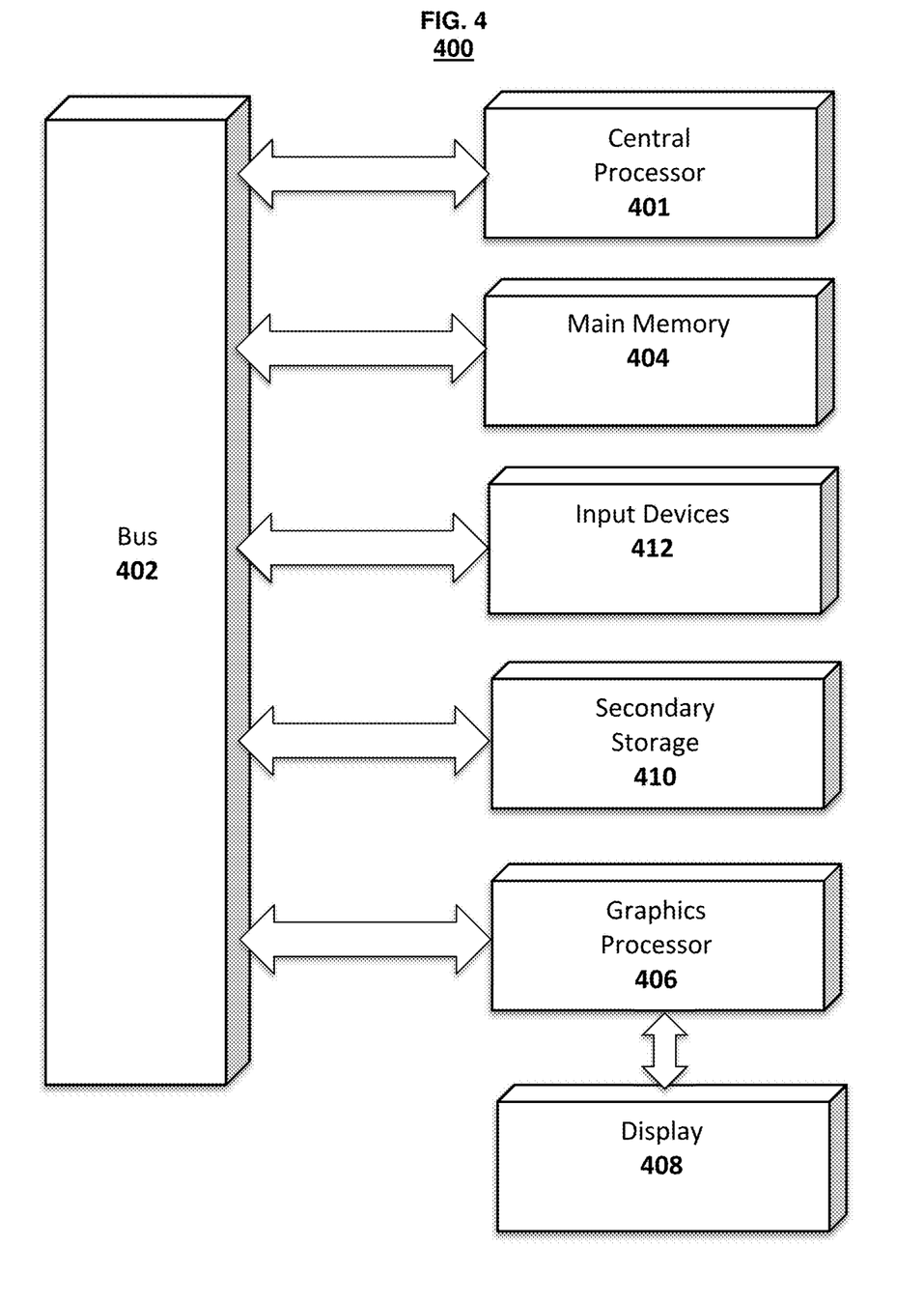
FIG. 4 depicts a system in which the processes, architecture, and/or functionality useful for denoising an ATAC-seq dataset in accordance with embodiments of the present disclosure may be implemented.

FIG. 4 depicts an exemplary system 400 in which the embodiments of the general denoising process 100, the neural network system architecture 200 and/or training and denoising engine functionalities 300 may be implemented. The system 400 includes at least one central processor 401 connected to a communication bus 402. The communication bus 402 may be implemented using any suitable protocol, such as PCI (Peripheral Component Interconnect), PCI-Express, AGP (Accelerated Graphics Port), HyperTransport, or any other bus or point-to-point communication protocol. The system 400 also includes a main memory 404. Control logic (software) and data are stored in the main memory 404 which may include random access memory (RAM). The system 400 also includes input devices 412, a graphics processor 406, and a display 408, such as a conventional CRT (cathode ray tube), LCD (liquid crystal display), LED (light emitting diode) display, and the like. User input may be received from the input devices 412, which can include, but is not limited to, keyboard, mouse, touchpad, microphone, and the like. In one embodiment, the graphics processor 406 may include a plurality of shader modules, a rasterization module, etc. Each of the foregoing modules may even be situated on a single semiconductor platform to form a graphics processing unit (GPU). As used herein, a single semiconductor platform may refer to a sole unitary semiconductor-based integrated circuit or chip, or to multi-chip modules with increased connectivity which simulate on-chip operation. The various modules may also be situated separately or in various combinations of semiconductor platforms per the desires of the user. The system 400 may also include a secondary storage 410, for example, a hard disk drive and/or a removable storage drive, representing a floppy disk drive, a magnetic tape drive, a compact disk drive, digital versatile disk (DVD) drive, recording device, universal serial bus (USB) flash memory.

Software instructions, computer programs, and/or computer control logic algorithms, may be stored in the system's main memory 404 and/or the secondary storage 410. Such software instructions, when executed, allow the system 400 to perform various functions. The main memory 404, secondary storage 410, and/or any other storage are examples of computer-readable media.

In one embodiment, the architecture and/or functionality of the various previous FIGS. 1-3 may be implemented in the context of the central processor 401, the graphics processor 406, an integrated circuit (not shown) that is capable of at least a portion of the capabilities of both the central processor 401 and the graphics processor 406, a chipset (i.e., a group of integrated circuits designed to work and sold as a unit for performing related functions, etc.), and/or any other integrated circuit.

In some embodiments, the architecture and/or functionality of FIGS. 1-3 may be implemented in the context of a general computer system, a circuit board system, an application-specific system, and/or any other desired system. For example, the system 400 may take the form of a desktop computer, laptop computer, server, workstation, embedded system, and/or any other type of logic. In some embodiments, the system 400 may take the form of various other devices including, but not limited to a personal digital assistant (PDA) device, a mobile phone device, a television, etc.

It is also contemplated, that in some embodiments, the system 400 may be coupled to a network (e.g., a telecommunications network, local area network (LAN), wireless network, wide area network (WAN) such as the internet, peer-to-peer network, cable network, or the like) for communication purposes.

In some embodiments, the methods and systems of denoising using neural networks as described in the present disclosure and exemplified by FIGS. 1-4, may be implemented, controlled, and/or otherwise utilized remotely via the internet, or other network system. For example, the system 400 could be hosted on one or more servers that could be accessed by remote users and used to denoise their ATAC-seq datasets. Accordingly, in some embodiments, users can upload their own ATAC-seq datasets for denoising using a trained neural network hosted on a server. Additionally, users can also upload their own suboptimal and/or model ATAC-seq datasets for further training of the neural network (e.g., reference learning) hosted on the remote servers. The user would then use the further trained neural network hosted on the servers to denoise their own experimental ATAC-seq datasets. Typically, users would download the denoised dataset output for further use locally, however in some embodiments the hosted system for denoising could include other tools for ATAC-seq dataset analysis such as databases of ATAC-seq datasets and/or other genomic data for use in various methods of genomic structure and function analysis.

Generally, the computing devices useful with the neural network based denoising processes and systems of the present disclosure can include any suitable combination of computing devices, including servers, interfaces, systems, databases, agents, peers, engines, controllers, modules, or other types of computing devices operating individually or collectively. At least one processor (e.g., GPU, CPU, ASIC, FPGA, DSP, x86, ARM, etc.) of the computing device is configured (or programmed) to execute software instructions stored on a computer readable tangible, non-transitory medium (e.g., hard drive, solid state drive, RAM, flash, ROM, etc.) and thereby carry out the processes involved in the methods of training and employing the neural network for denoising data.

The software instructions configure or program the computing device to provide the denoising of ATAC-seq datasets functionality can be prepared using standard programming tools. For example, the ATAC-seq data manipulations can be programmed using the source code in the "ATAC-Seq pipeline" software tools available from the ENCODE Project site, and the CNN configuration can be programmed with the software tools, Keras (v.2.1.3) and Tensorflow (v.1.4.0). Generally, the software instructions are embodied as a computer program product comprising a non-transitory, tangible computer readable medium storing the instructions that cause a processor of the computing device to execute the steps of the denoising processes disclosed herein.

Additionally, the methods of the present disclosure can be carried out using standard protocols and algorithms for data exchange between servers, systems, databases, or interfaces in implementing the processes. For example, data exchange used in implementing the methods and systems of the present disclosure can be conducted over a packet-switched network, a circuit-switched network, the internet, LAN, WAN, VPN (or other type of networks) using protocols based on HTTP, HTTPS, AES, public-private key exchanges, web service APIs, financial transaction protocols, or other electronic information exchange methods.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Use of a Neural Network to Denoise Suboptimal ATAC-Seq Datasets

This example illustrates the use of methods and systems of the present disclosure to prepare a trained neural network and use it for denoising an ATAC-seq dataset.

ATAC-Seq Datasets:

Suboptimal and model datasets from ATAC-seq used in the training and testing of the denoising system are obtained by carrying out ATAC-seq experiments using well-known techniques or can be obtained from the publicly available databases such as ENCODE Project (www.encodeproject.org). ATAC-seq datasets used for training and testing the denoising process are arbitrarily chosen from experimental datasets obtained from different types of human tissue.

Protocols, materials, reagents, and experimental parameters used to prepare tissue samples and carry out the ATAC-seq experiments protocols are available at the ENCODE Project site (www.encodeproject.org). Additionally, workflow and scripts for processing the sequence reads and preparing the final ATAC-seq datasets are provided at the ENCODE Project site for each experiment.

Briefly, the ATAC-seq datasets are from experimental studies carried out using standard ATAC-seq protocols, materials, and methods well-known in the art and described in e.g., Buenrostro 2013, and U.S. Pat. No. 10,059,989 (Giresi et al.). Generally, the reads of the ATAC-seq adapter sequences are determined using an Illumina HiSeq 4000 next generation sequencer. The suboptimal datasets consist of five million reads (N=5 M) on average, while the high-quality model datasets consist of at 20 million to 50 million NGS reads (N=20 M to 50 M) on average.

The datasets are prepared by mapping the ATAC-seq reads to the human reference genome to generate a histogram including each bp position spanning the full length of the human genome. Before use in training a neural network or in an experimental ATAC-seq data denoising process, the ATAC-seq datasets are partitioned into non-overlapping segments of 4000 bp in length. The complete set of non-overlapping 4000 bp segments included every bp position of the genome that was in the original dataset. Additionally, any DNA sequence information (i.e., the identity of the specific base at each position) is excluded in the segments used for training or denoising.

To prepare the datasets for neural network training or for use in experimental denoising, standard data processing software tools and scripts are used as described in the "ATAC-Seq pipeline v1 specifications" available from the ENCODE Project site. Briefly, the input to the data processing is a "barn" file which is processed from a "fastq" file using ENCODE's ATAC-seq processing pipeline. The "bedtools genomecov" tool from the pipeline is used to generate a "bedGraph" file with ATAC-seq counts at each position. The "bedGraph" file is converted to "bigwig" format using the "WigToBigWig" binary from "kentUtils."

Neural network configuration and training: The configuration and training of the neural network is implemented in software using Keras version 2.1.3 with Tensorflow backend version 1.4.0. The configuration of the neural network is a CNN that employs a sequence of three convolution layers each followed by a ReLU (residual connection) layer. The receptive field sizes of the first, second, and third convolution layers is 100, 100, and 300, respectively, with the successive layers using 15, 15, and 1 filters, respectively. Additionally, a residual connection is included between the third convolution layer and the final ReLU. The residual connection functions to sum the output of the third convolution layer with the input suboptimal data. This allows the output to better focus on the difference between the suboptimal ATAC-seq input and the model ATAC-seq dataset. The configuration of the CNN used for denoising is completely convolutional and did not include any recurrent layers.

Neural network training is carried out on the suboptimal ATAC-seq dataset with a high-quality dataset as model and using standard training methods with a simple mean square loss function. Briefly, a segment of the suboptimal ATAC-seq dataset obtained from stomach tissue is input into the neural network. A portion of the experimental stomach tissue dataset is held out for used in testing the denoising process using the trained neural network. The transformed output of the neural network is then mapped to the corresponding segment of the model ATAC-seq dataset and the mean square error loss function of the mapping is calculated. This training process is iterated for each segment until the loss function is minimized across the full-length of the genome. The trained neural network resulting upon minimizing the loss function is thus optimized for demising an ATAC-seq dataset.

Denoising Test Using Held Out Dataset:

The optimized neural network can be used to denoise new experimental ATAC-seq datasets, even suboptimal experimental datasets that were not used in training the neural network. A suboptimal ATAC-seq dataset of 5 M reads on average obtained from stomach tissue, and a model 50 M read dataset from the same stomach tissue cells are used. These suboptimal and model sample stomach tissue datasets cover chromosomal regions of the genome that were not used in training the optimized neural network. The suboptimal sample dataset is partitioned into 4000 bp non-overlapping segments and the segments transformed using the optimized neural network resulting from training as described above. The denoised segments of the suboptimal 5 M read ATAC-seq dataset output from the optimized neural network are reassembled into a full ATAC-seq data histogram for comparison with the model 50 M read dataset.

Figure 5:
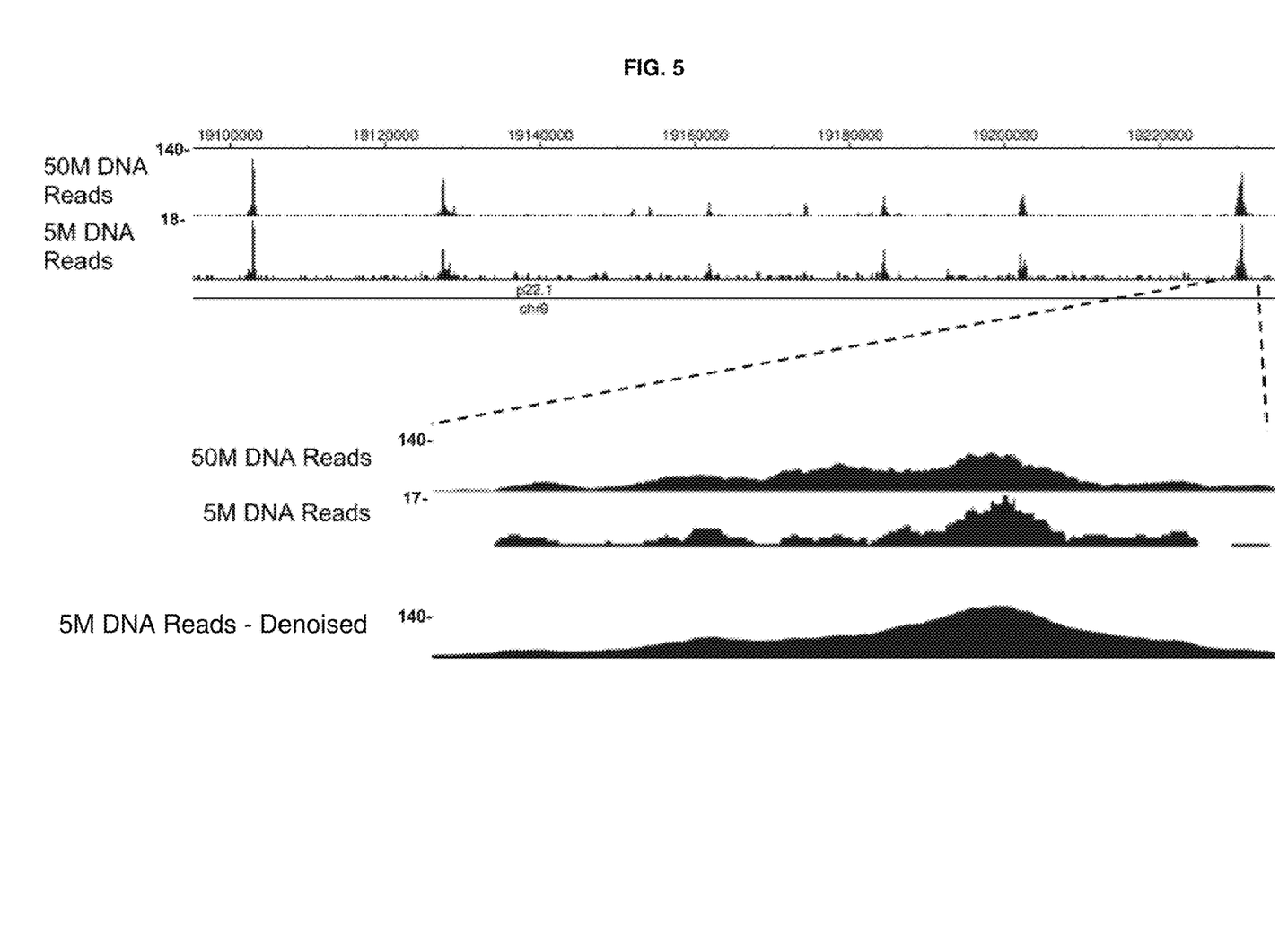
FIG. 5 depicts a high-quality model ATAC-seq dataset histogram (average of 50 M DNA reads), and a suboptimal low-quality (average of 5 M DNA reads) obtained from stomach tissue cells as described in Example 1. The two top histograms depict an expanded range of the model and suboptimal ATAC-seq dataset histograms mapped to chromosome 9. The three lower histograms correspond to an enlargement of a 4000 bp segment of the histograms as well as the suboptimal histogram that has been denoised using the denoising process with a neural network trained as described in Example 1.

Results:

FIG. 5 shows the ATAC-seq data histograms of the suboptimal (average 5 M reads) and model (average of 50 M reads) datasets obtained from the stomach tissue cell samples, as well as, blow-outs from the larger histogram showing the improvement resulting from the denoising process using the trained neural network. Additionally, a Pearson's correlation was calculated for each of the initial suboptimal ATAC-seq dataset and the denoised suboptimal ATAC-seq dataset when compared to the model ATAC-seq dataset obtained with 50 M reads. Without denoising, the Pearson's correlation between the suboptimal 5 M read dataset and the model 50 M read dataset was 86.6%. With denoising using the optimized neural network, the Pearson's correlation between the suboptimal and model dataset increased significantly to 93.8%. In order quantify the significance of this increase, the number of NGS reads needed to achieve 93.8% correlation with a 50 M dataset was determined to be 20 M. This demonstrates that the denoising method can save the time and cost of obtaining an additional 15 M NGS reads as well as the compute time used to map those reads to the reference genome.

Example 2: Use of Neural Network Trained on ATAC-Seq Data from a Different Cell-Type to Denoise Suboptimal ATAC-Seq Data This example illustrates the use of methods for denoising an ATAC-seq dataset across cell-types. Briefly, a trained neural network is prepared by training with sample suboptimal ATAC-seq datasets obtained from a range of human tissue types using the same general methods described in Example 1. The optimized neural network then is used to denoise suboptimal ATAC-seq datasets obtained from two human tissue types not used in training the optimized.

ATAC-Seq Datasets:

Suboptimal (5 M reads) and model (50 M reads) ATAC-seq datasets are obtained from ATAC-seq experiments carried out on samples from the following human tissues: coronary artery, right atrium auricular region, stomach, testis, tibial nerve, left heart ventricle, and Peyer's patch.

Neural Network Configuration and Training:

The neural network architecture is as described in Example 1. Training also is carried out as in Example 1 using suboptimal ATAC-seq datasets from the following five tissue samples: coronary artery, right atrium auricular region, stomach, testis, and tibial nerve. The corresponding model dataset from each of the five tissue types is used as model during the training. The same simple mean square loss function is used for training as described in Example 1.

Denoising ATAC-Seq Datasets:

The trained neural network resulting from the above-described training is used to denoise suboptimal ATAC-seq datasets from the following two tissues samples not used in the training datasets: left heart ventricle and Peyer's patch. The method of denoising is as described in Example 1.

Results:

The Pearson's correlation coefficient between the suboptimal (5 M read) and the model (50 M read) datasets for each of the left heart ventricle and Peyer's patch, were 55% and 60%, respectively. With denoising using the neural network trained with other tissue type samples, correlation coefficients between the suboptimal (but denoised) and model datasets increased substantially to 69% and 77%, respectively. These significant increases in ATAC-seq dataset quality achieved using a neural network trained on samples obtained from different tissue types demonstrates the surprising flexibility and robustness of the application of these deep-learning methods and systems of the present disclosure to this type of data.

While the foregoing disclosure of the present invention has been described in some detail by way of example and illustration for purposes of clarity and understanding, this disclosure including the examples, descriptions, and embodiments described herein are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedures to those described herein. All such equivalents are to be understood to be within the scope of the present disclosure and are covered by the appended claims.

Additional embodiments of the invention are set forth in the following claims.

What is claimed is:

1. A computer-implemented method for denoising ATAC-seq data comprising:
   partitioning an ATAC-seq dataset into a plurality of segments representing a genome, wherein the segments comprise ATAC-seq counts at each base pair position and exclude base identity at each base pair position; and
   using one or more neural networks to identify the ATAC-seq dataset based, at least in part, on the plurality of segments.

2. The method of claim 1, wherein the segments have a length of about 1000 bp to about 25,000 bp.

3. The method of claim 1, wherein the neural network comprises at least three successive convolutional layers followed by a residual connection that sums the ATAC-seq counts at each base pair position of each segment input with the final convolutional layer output.

4. The method of claim 3, wherein each convolutional layer and the residual connection is followed by an ReLU layer.

5. The method of claim 3, wherein the convolutional layers have a receptive field size of 100 to 10,000.

6. The method of claim 3, wherein the convolutional layers use a number of filters selected from 1 to 100.

7. The method of claim 3, wherein the neural network comprises 3 successive convolutional layers of receptive field size 100, 100, and 300, respectively, and using 15, 15, and 1 filters, respectively.

8. The method of claim 1, wherein the method further comprises training the neural network, wherein training comprises:
   partitioning a suboptimal ATAC-seq dataset and a model ATAC-seq dataset into a plurality of segments representing a genome, wherein the segments comprise ATAC-seq counts at each base pair position and exclude base identity at each base pair position; and
   transforming the segments of the suboptimal ATAC-seq dataset with the neural network, using a loss function to compare the neural network output to the model ATAC-seq dataset segments, and adjusting the neural network until the loss function is minimized.

9. The method of claim 8, wherein the loss function is a mean square error loss function.

10. The method of claim 8, wherein the model ATAC-seq dataset relative to the suboptimal ATAC-seq dataset comprises at least 4-fold increased number of reads of ATAC-seq counts.

11. A system for denoising ATAC-seq data comprising:
    a processor, a memory device, and a denoising engine executable on the processor according to software instructions stored in the memory device, wherein the denoising engine is configured to:
    partition an ATAC-seq dataset into a plurality of segments representing a genome, wherein the segments comprise ATAC-seq counts at each base pair position and exclude base identity at each base pair position; and
    using one or more neural networks to identify the ATAC-seq dataset based, at least in part, on the plurality of segments.

12. The system of claim 11, wherein the segments have a length of about 1000 bp to about 25,000 bp.

13. The system of claim 12, wherein each convolutional layer and the residual connection is followed by an ReLU layer.

14. The system of claim 11, wherein the neural network comprises at least three successive convolutional layers followed by a residual connection that sums the ATACseq counts at each base pair position of each segment input with the final convolutional layer output.

15. The system of claim 14, wherein the convolutional layers have a receptive field size of 100 to 10,000.

16. The system of claim 14, wherein the convolutional layers use a number of filters selected from 1 to 100.

17. The system of claim 14, wherein the neural network comprises 3 successive convolutional layers of receptive field size 100, 100, and 300, respectively, and using 15, 15, and 1 filters, respectively.

18. The system of claim 11, wherein the system further comprises
    a training engine executable on the processor according to software instructions stored in the memory device, wherein the training engine is in communication with the denoising engine and is configured to:
    partition a suboptimal ATAC-seq dataset and a model ATAC-seq dataset into a plurality of segments representing a genome, wherein the segments comprise ATAC-seq counts at each base pair position and exclude base identity at each base pair position; and
    transform the segments of the suboptimal ATAC-seq dataset with the neural network, using a loss function to compare the neural network output to the model ATAC-seq dataset segments, and adjusting the neural network until the loss function is minimized.

19. A non-transitory computer-readable medium for denoising ATAC-seq data comprising instructions for denoising an ATAC-seq dataset that, when executed by a processor, cause the processor to perform one or more steps comprising:
    partitioning an ATAC-seq dataset into a plurality of segments representing a genome, wherein the segments comprise ATAC-seq counts at each base pair position and exclude base identity at each base pair position; and using one or more neural networks to identify the ATAC-seq dataset based, at least in part, on the plurality of segments.

20. The non-transitory computer-readable medium of claim 19, wherein the medium further comprises instructions for:

partitioning a suboptimal ATAC-seq dataset and a model ATAC-seq dataset into a plurality of segments representing a genome, wherein the segments comprise ATAC-seq counts at each base pair position and exclude base identity at each base pair position; and transforming the segments of the suboptimal ATAC-seq dataset with the neural network, using a loss function to compare the neural network output to the model ATAC-seq dataset segments, and adjusting the neural network until the loss function is minimized.

* * * * *